US00PP23114P2

(12) United States Plant Patent
Nielsen

(10) Patent No.: US PP23,114 P2
(45) Date of Patent: Oct. 16, 2012

(54) *DAHLIA* PLANT NAMED 'DAATTEN'

(50) Latin Name: ***Dahlia* hybrid**
Varietal Denomination: DAATTEN

(75) Inventor: Rune Harboe Nielsen, Groennegyden (DK)

(73) Assignee: Dalina APS, Odense N (DK)

( * ) Notice: Subject to any disclaimer, the term of this patent is extended or adjusted under 35 U.S.C. 154(b) by 0 days.

(21) Appl. No.: 13/067,059

(22) Filed: May 5, 2011

(51) Int. Cl.
*A01H 5/00* (2006.01)

(52) U.S. Cl. ..... Plt./321

(58) Field of Classification Search ..... Plt./321
See application file for complete search history.

(56) References Cited

OTHER PUBLICATIONS

Printout of application information from Community Plant Variety Office (CPVO) website for corresponding CPVO application No. 2011/0690 filed Mar. 18, 2011 (1 page). (http://www.cpvoextranet.cpvo.europa.eu).

*Primary Examiner* — Kent L Bell
(74) *Attorney, Agent, or Firm* — Foley & Lardner LLP

(57) ABSTRACT

A new distinct cultivar of *Dahlia* plant named 'DAATTEN', characterized by its compact growth with cylindrical upright to slightly spreading shape; stiff and strong lateral stems and thick single and compound leaves with up to 3 leaflets; color of mature leaves RHS 147A (upper side), RHS 191B (Underside); compound leaves 12-18 cm in length, and 12-15 cm in width and single leaves 6-13 cm in length and 6-9 cm in width; composite inflorescence heads 11-12 cm in diameter with a large number of ray florets (about 120 to 140); and white ray florets (RHS 155B to 155C) with small area of yellow near base (RHS 1B).

7 Drawing Sheets

Latin name of the genus and species of the claimed plant: *Dahlia* hybrid.

Variety denomination: 'DAATTEN'.

BACKGROUND OF THE INVENTION

The present invention relates to a new and distinct cultivar of *Dahlia* plant, botanically known as *Dahlia Cav.*, of the Compositae (Asteraceae) family, hereinafter referred to by the cultivar name 'DAATTEN'.

The new *Dahlia* cultivar is a product of a planned breeding program conducted by the inventor, Rune Nielsen, in Stige, Denmark. The objective of the breeding program is to develop a new *Dahlia* cultivar with an upright, strong and healthy growth habit, suitable for large scale container production and with good garden performance; fully double inflorescences creating globular-shaped inflorescence head (composite inflorescence heads with many ray florets) with an attractive inflorescence color.

The new *Dahlia* cultivar originated from a cross, made in a controlled breeding program by the inventor in 2006, in Stige, Denmark. The female or seed parent is a white colored *Dahlia* variety designated 4416B (not patented). The male or pollen parent is a yellow colored *Dahlia* variety designated 5218A (not patented).

Asexual reproduction of the new *Dahlia* cultivar by terminal cuttings was first performed in November, 2007 in Stige, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DAATTEN', which in combination distinguish this *Dahlia* as a new and distinct cultivar:

1. Compact cultivar, with cylindrical upright to slightly spreading shape;
2. Compact cultivar with stiff and strong lateral stems and thick single and compound leaves, with up to 3 leaflets. Color of mature leaves yellow-green (RHS 147A) (upper side), greyed-green (RHS 191B) (Underside);
3. Compound leaves 12-18 cm in length, and 12-15 cm in width. Single leaves 6-13 cm in length and 6-9 cm in width;
4. Composite inflorescence heads, 11-12 cm in diameter, with a large number of ray florets (about 120 to 140); and
5. White ray florets (RHS 155B to 155C) with small area of yellow near base (RHS 1B).

Plants of the new *Dahlia* 'DAATTEN' differ from plants of the parents, 4416B (unpatented) and 5218A (unpatented) in the traits described in Table 1.

TABLE 1

Comparison with Parent Varieties

| Trait | New Cultivar 'DAATTEN' | Female Parent 4416B (unpatented) | Male Parent 5218A (unpatented) |
|---|---|---|---|
| Plant Size | | | |
| Height: | About 25-30 cm. | About 25-30 cm. | About 30-45 cm. |
| Diameter: | About 40-45 cm. | About 35-40 cm. | About 40-45 cm. |
| Overall Plant Shape: | Cylindrical, upright, with basal branching. Inflorescences in composite heads. | Cylindrical, upright, with basal branching. Inflorescences in composite heads. | Upright to spreading, with basal branching. Inflorescences in composite heads. |
| Stem | | | |
| Length: | 8-18 cm. | 8-16 cm. | 8-18 cm. |
| Diameter: | 8-12 mm | 8-12 mm | 8-12 mm |

TABLE 1-continued

| Comparison with Parent Varieties | | | |
|---|---|---|---|
| Trait | New Cultivar 'DAATTEN' | Female Parent 4416B (unpatented) | Male Parent 5218A (unpatented) |
| Strength: | Stiff and strong. | Stiff and strong. | Medium strong. |
| Color: | RHS 144A (yellow-green). | RHS 144A (yellow-green). | RHS 144A (yellow-green). |
| Number of Inflorescence heads per Plant: | About 15. | About 12. | About 15. |
| Inflorescence (Capitalum) Diameter: | About 11-12 cm. | About 10 cm. | About 12 cm. |
| Color of ray florets Upper side: | RHS 155B to 155C (white), RHS 1B (green-yellow) near the base. | RHS 155B (white). | Yellow cactus flower. |

Of the many commercial cultivars known to the present inventor, the most similar in comparison to the new *Dahlia* 'DAATTEN' is the *Dahlia* cultivar 'Gallery Art Fair', in the characteristics described in Table 2:

TABLE 2

| Comparison with Comparison Variety | | |
|---|---|---|
| Trait | New Cultivar 'DAATTEN' | Comparison Cultivar 'Gallery Art Fair' |
| Plant Size | | |
| Height: | About 25-30 cm. | About 25-30 cm. |
| Diameter: | About 40-45 cm. | About 40-45 cm. |
| Overall Plant Shape: | Cylindrical, upright, with basal branching. Inflorescences in composite heads. | Cylindrical, upright, with basal branching. Inflorescences in composite heads. |
| Stem | | |
| Length: | 8-18 cm. | 8-18 cm. |
| Diameter: | 8-12 mm | 8-12 mm |
| Strength: | Stiff and strong. | Stiff and strong. |
| Color: | RHS 144A (yellow-green). | RHS 144A (yellow-green). |
| Leaves: | | |
| Texture | Rugose. | Glabrous, shining. |
| Colour mature upperside: | RHS 147A (yellow-green) | RHS N189A (greyed-green) |
| Number of Inflorescence heads per Plant: | About 15. | About 10. |
| Bud color | RHS 144B (yellow-green) | RHS 151C (yellow-green) |
| Inflorescence (Capitalum) Diameter: | About 11-12 cm. | About 12 cm. |
| Color of ray florets Upper side: | RHS 155B to 155C (white), RHS 1B (green-yellow) near the base. | RHS 155B/155C (white), RHS 1B (green-yellow) near the base. |

BRIEF DESCRIPTION OF THE PHOTOGRAPHS

The accompanying photographs illustrate the overall appearance of the new *Dahlia* 'DAATTEN' showing the colors as true as is reasonably possible with colored reproductions of this type. Colors in the photographs may differ slightly from the color value cited in the detailed botanical description, which accurately describe the color of 'DAATTEN'.

DETAILED BOTANICAL DESCRIPTION

Figure 1:
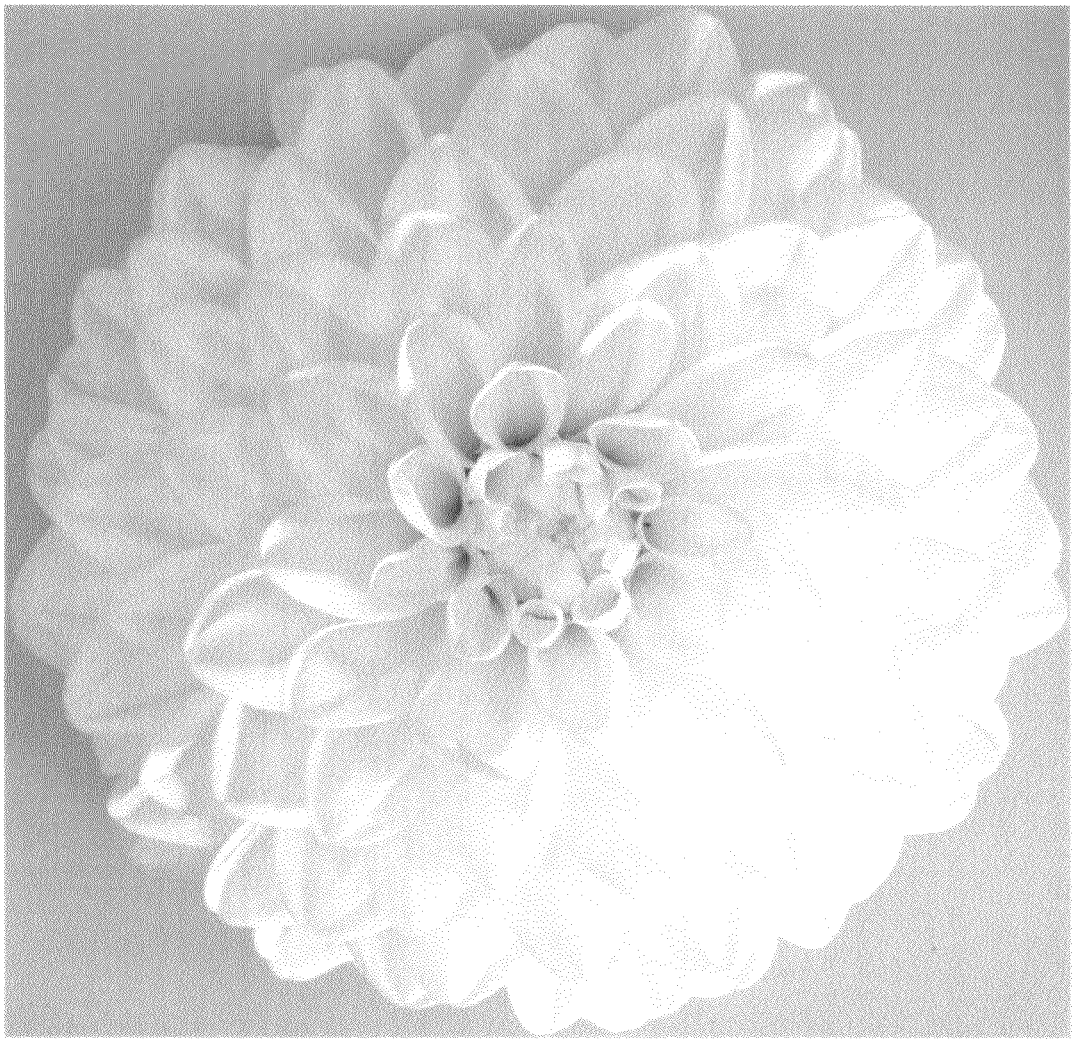
FIG. 1 shows a close-up view of the composite inflorescence head from 'DAATTEN'.
Figure 2:
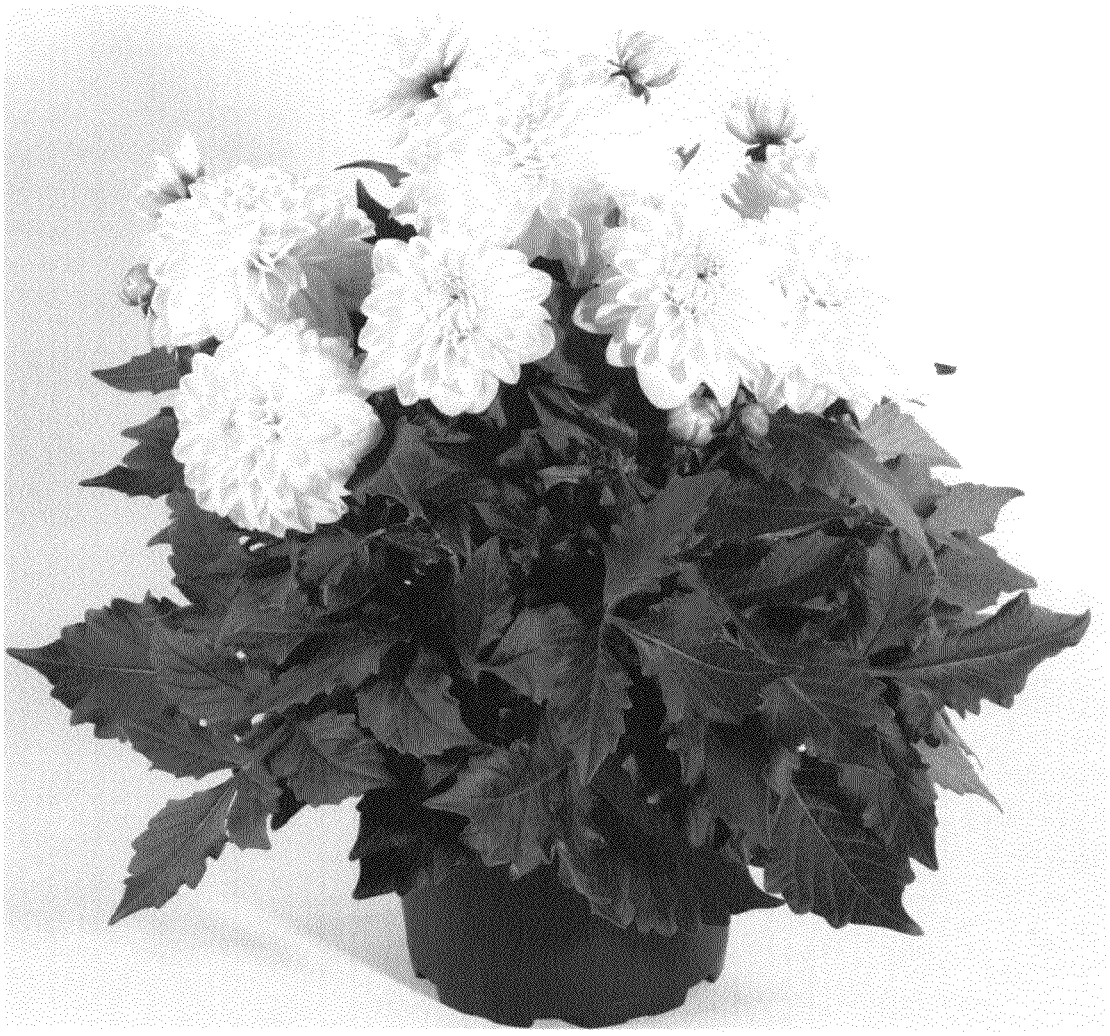
FIG. 2 shows a side view perspective of a typical flowering plant of 'DAATTEN' in a 19 cm pot, at 12 weeks of age after potting the young plant.
Figure 3:
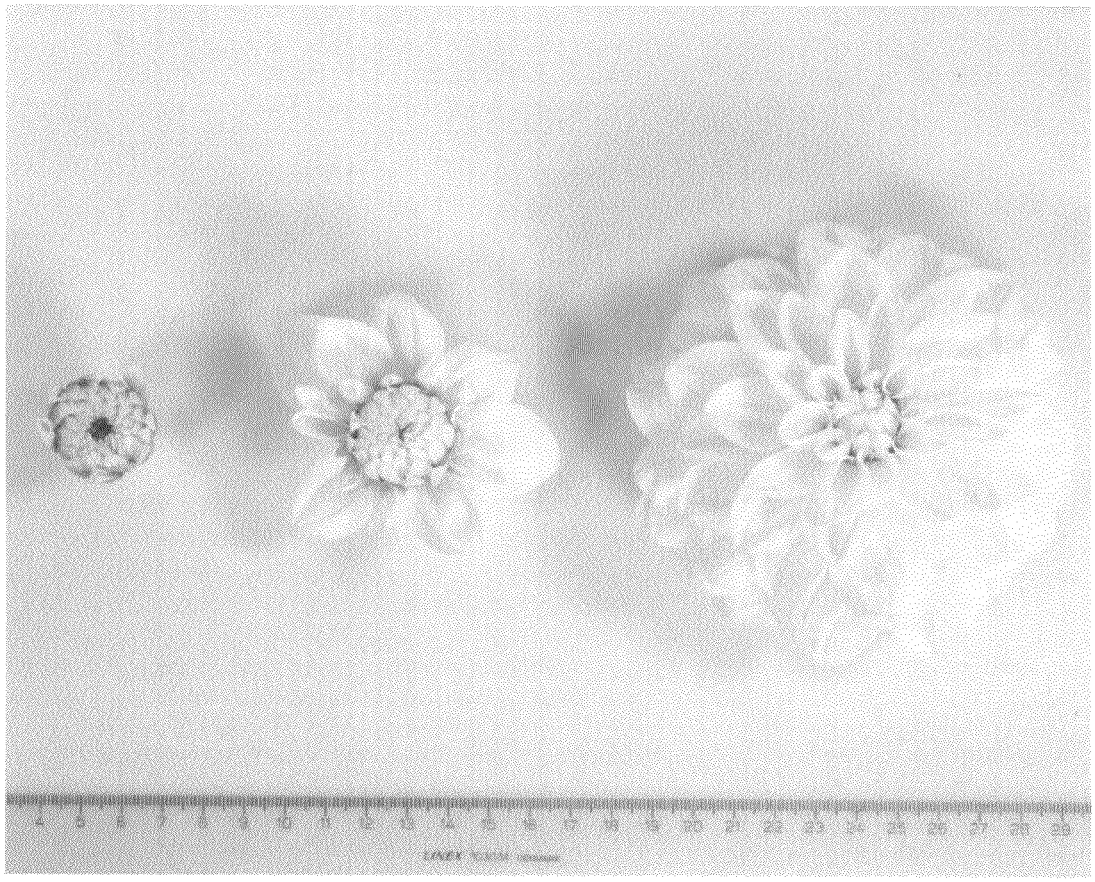
FIG. 3 shows a close-up view of different development stages of the composite inflorescence head of 'DAATTEN'.
Figure 4:
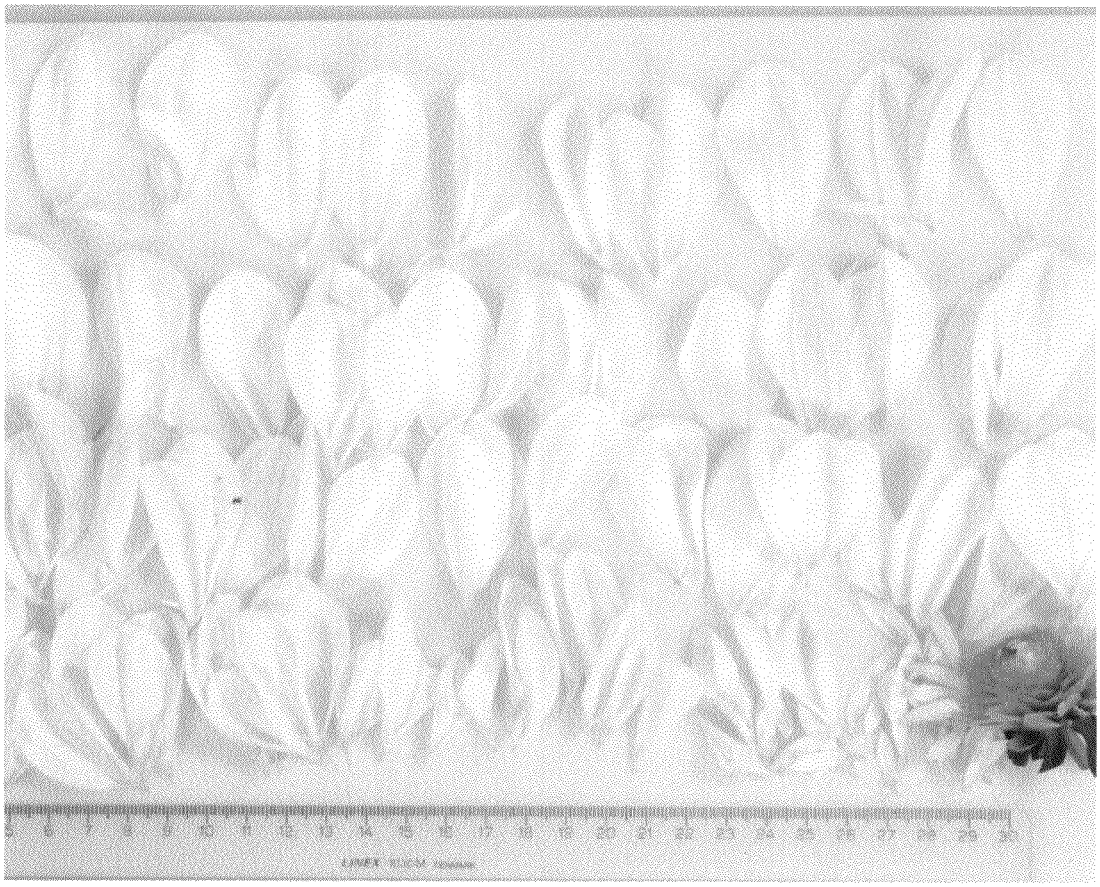
FIG. 4 shows a close-up view of the 120-140 ray florets from one composite inflorescence head of 'DAATTEN'
Figure 5:
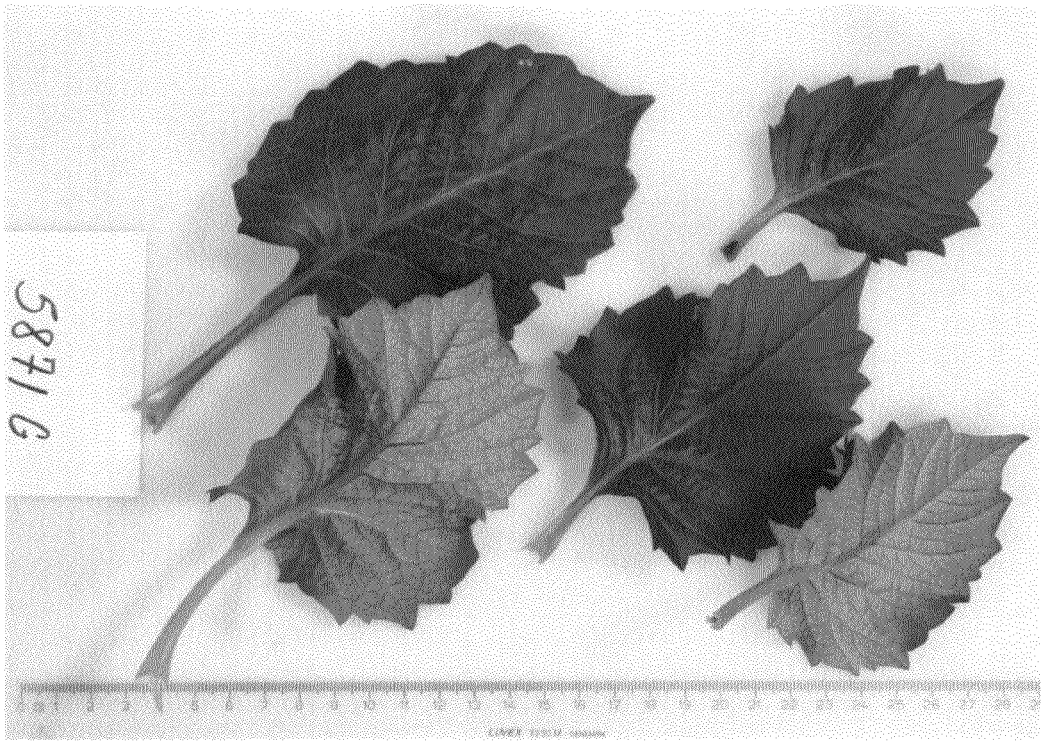
FIG. 5 shows a close-up view of the different single leaf sizes of 'DAATTEN', (Breeders Reference: 5871G).
Figure 6:
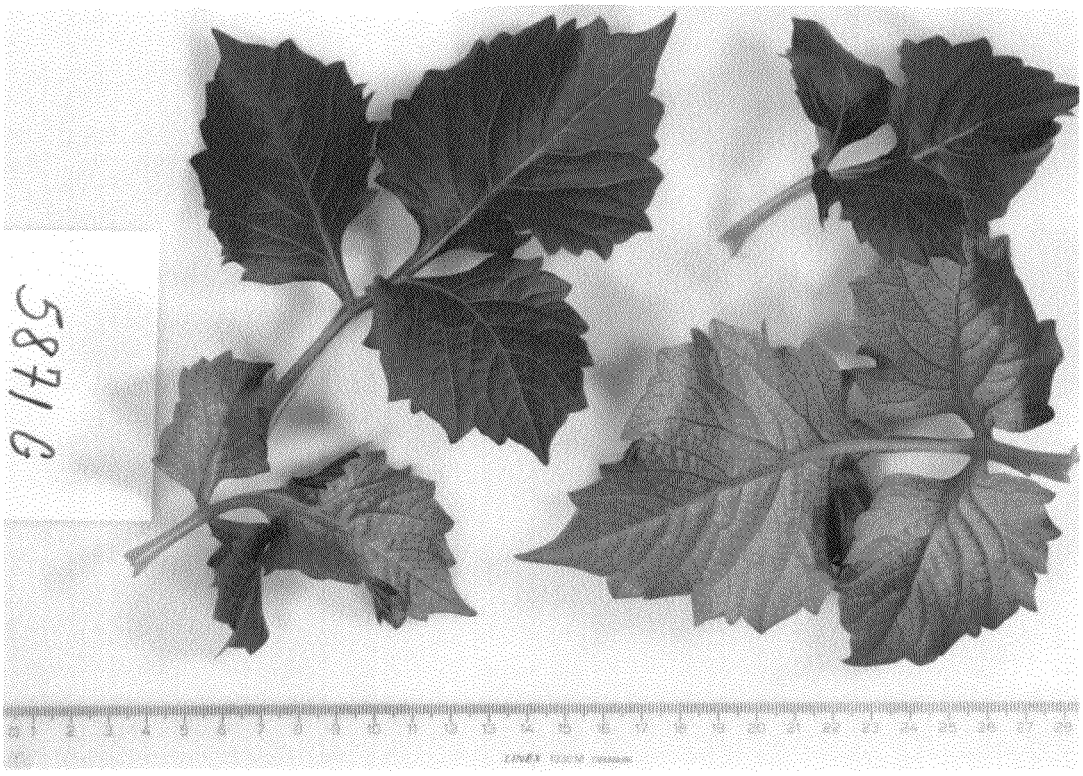
FIG. 6 shows a close-up view of the different compound leaf sizes of 'DAATTEN', (Breeders Reference: 5871G).
Figure 7:
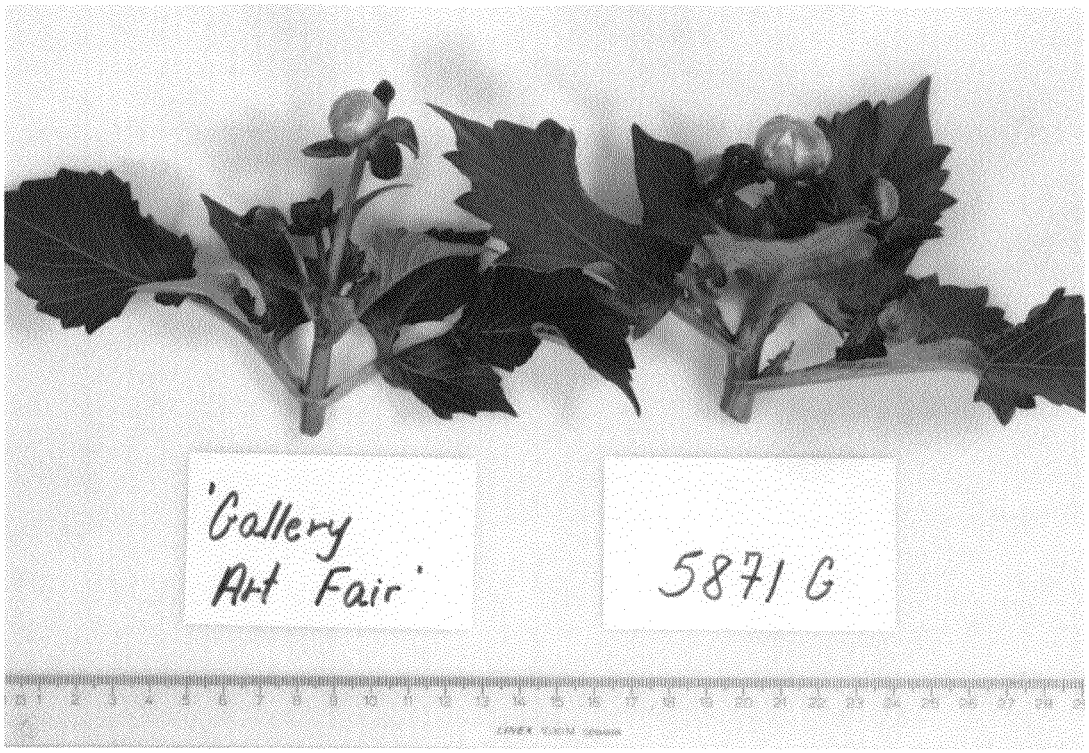
FIG. 7 shows a comparison between 'Gallery Art Fair' and 'DAATTEN', (Breeders reference: 5871G).

The new *Dahlia* 'DAATTEN' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Dahlia* 'DAATTEN' as grown in a protected environment in a glass greenhouse in Fyn, Odense, Denmark, under conditions which closely approximate those generally used in commercial practice. During propagation, conducted in a glasshouse, vegetative cuttings were planted in small propagation pots with peat as substrate, and then placed in a plastic tunnel averaging about 21° C. and received photoperiodic treatments of 18 hours. Supplementary light was given when natural light fell below 3000-4000 Lux. Rooting occurred about 12 days after planting. In third week after planting the cutting, young plants were potted in an 19 cm pot in a glass covered greenhouse, maintained at 18° C. to 22° C. during the day, and at 17° C. to 19° C. during the night. Photoperiodic treatments were continued at 18 hours, and supplementary light was given when natural light fell below 3000-4000 Lux. Irrigation was done with water. The EC measured in the soil was maintained between 2.0 to 3.0. One week after potting, the first growth regulation was given: a spray with 85% daminozide, 0.2%, 40-100 ml/m2. During the production time, 9 additional sprayings were given with 85% daminozide, 0.2%, 40-100 ml/m2.

Color references are made to The Royal Horticultural Society Colour Chart (R.H.S.), 2001 edition, except where general colors of ordinary significance are used. Color values were taken under March daylight conditions at approximately 12:00 PM and 2:00 PM in Fyn, Odense, Denmark. The age of the 'DAATTEN' plants described is 15 weeks (including propagation time).

Classification:

*Botanical.—Dahlia* hybrid.

Parentage:

*Female or seed parent.—Dahlia* variety designated 4416B (Unpatented).

*Male or pollen parent.—Dahlia* variety designated 5218A (Unpatented).

Propagation:

*Type.*—Vegetative terminate cuttings.

*Time and temperature to initiate roots.*—About 9 to 12 days at 21° C. in tunnels or flat covered in a greenhouse.

*Time and temperature to produce a rooted young plant*.—About 28 days at 21° C. during rooting phase, followed by 18° C.

*Rooting Habit*.—Fine, fibrous; Color of root: RHS 158A Yellow-white.

*Tuber development*.—Plants might develop tubers in late fall when planted outside.

Plant description:

*General appearance and form*.—Cylindrical, upright, with basal branching. Inflorescences in composite heads.

*Growth rate*.—Growing about 4 to 6 cm per week during production period.

*Plant height* (*from soil level to top of plant plane*).—About 25 cm to 30 cm.

*Plant width* (*spread*).—About 40 cm to 45 cm.

*Crop time to produce a mature flowering plant*.—It requires 3 to 4 weeks to produce a young plant in a 35 mm propagation plug. After potting 9 to 12 weeks are required to produce finished flowering plants in 19 cm pots.

Stem:

*Shape*.—Round.

*Length*.—About 8 cm to 18 cm.

*Diameter*.—About 8 mm to 12 mm.

*Strength*.—Stiff and strong.

*Aspect*.—Upright to outward.

*Texture*.—Smooth and glabrous, slightly furrowed.

*Color*.—Mature: RHS 144A. Immature: RHS 144A.

Branches:

*Branching habit*.—Basal branching with small lateral branches.

*Number of basal branches per plant*.—About 3-5 (when pinched above 3 pair of leaves).

*Length* (*including inflorescence*).—About 8 cm to 18 cm.

*Diameter*.—About 8 mm to 12 mm.

*Strength*.—Stiff and strong.

*Aspect*.—Upright to spreading.

*Texture*.—Smooth and glabrous.

*Color*.—Mature: RHS 144A. Immature: RHS 144A.

*Internode length*.—About 15 to 20 mm.

*Internode color*.—RHS 144A.

Foliage description:

*Type*.—Lower leaves: Single. Middle leaves: Compound, 3 lobed. Upper leaves: Single.

*Number of leaves per branch*.—About 8 to 12 per branch.

*Color of leaves* (*leaves and leaflets*).—Color of upper side (mature) RHS 147A. Color of underside (mature) RHS 191B. Color of upper side (immature) RHS 138A. Color of underside (immature) 138A.

*Venation* (*leaves and leaflets*).—Pattern: Pinnate. Color of upper side: RHS 148A. Color of underside: RHS 146A.

Compound leaves:

*Number of leaflets per compound leaf*.—3.

*Length of compound leaf*.—12 cm to 18 cm.

*Width of compound leaf*.—12 cm to 15 cm.

*Petiole of compound leaves*.—Shape: Semi circular, with deep furrow on adaxial side. Length: 2.5 cm to 5 cm. Diameter: 3 mm to 6 mm. Texture: Smooth and glabrous. Color: RHS 146B.

*Leaflets of compound leaf*.—Terminal leaflet quantity: 1. Terminal leaflet length: 8 cm to 13 cm. Terminal leaflet width: 5 cm to 8 cm. Terminal leaflet shape: Ovate. Terminal leaflet shape at apex: Acuminate. Terminal leaflet shape at base: Cordate to rounded. Terminal leaflet margin: Dentate. Terminal leaflet texture (both sides): Rugose. Rachis length: 1 cm to 2 cm. Rachis Diameter: 3 mm to 4 mm. Rachis color: RHS 146B. Lateral leaflet quantity: 2. Lateral leaflet length: 6 cm to 8 cm. Lateral leaflet width: 4 cm to 6 cm. Lateral leaflet overall shape: Ovate. Lateral leaflet shape at apex: Acuminate (asymmetric). Lateral leaflet shape at base: Rounded.

*Lateral leaflet margin*.—Dentate.

*Lateral leaflet texture* (*both sides*).—Rugose.

Simple leaves:

*Simple leaves overall shape*.—Ovate.

*Simple leaves shape at apex*.—Acuminate.

*Simple leaves shape at base*.—Cordate to rounded.

*Simple leaves length*.—6 cm to 13 cm.

*Simple leaves width*.—6 cm to 9 cm.

*Simple leaves margin*.—Dentate.

*Simple leaves texture*.—Rugose.

*Petiole shape*.—Semi circular, with deep furrow on adaxial side.

*Petiole length*.—2.5 cm to 5 cm.

*Petiole diameter*.—3 mm to 6 mm.

*Petiole texture*.—Smooth and glabrous.

*Petiole color*.—RHS 146B.

Inflorescence description:

*Natural flowering season*.—Grown outside as a bedding plant, flowering occurs continuously during growing season from spring to autumn (In Denmark, from June to beginning of October). Plants can be brought to flower anytime when grown under the recommended greenhouse conditions.

*Time to flower*.—60 to 80 days from potting a young plant until flowering.

*Inflorescence longevity on the plant*.—Inflorescence will maintain good color and substance for about 6-10 days; however, the longevity of individual inflorescence is highly dependent on temperature and light conditions. Inflorescence persistent.

*Type*.—Composite inflorescence heads.

*Arrangement and shape*.—Persistent, single, composite inflorescences from leaf axils. Disc and ray florets arranged acropetally in a composite inflorescence head. Upright, slightly spreading. Terminal young inflorescence head/buds initially 0-20°. Buds from axillary shoots 1-60°. When flower opens 0-30°.

*Quantity of inflorescences heads*.—Freely flowering; about 15 buds and open inflorescences per plant.

*Fragrance*.—None.

*Bud* (*inflorescences head*).—Rate of opening (from showing color to fully open): 4 to 10 days. The rate of opening is highly dependent on temperature and light conditions. Length: About 12-14 mm. Diameter: About 16-22 mm. Shape: Flat globular. Texture: Glabrous, shining. Color RHS 144A developing into RHS 144B.

*Peduncle*.—From both terminate and axillary shoots. Length: About 4-12 cm. Diameter: About 3-5 mm. Angle: About 0-20° from vertical. Strength: Stiff and strong. Texture: Glabrous. Color: RHS 144A.

*Inflorescence head*.—Depth (height): 6-7 cm. Diameter: 11-12 cm.

*Ray florets*.—Arrangement: Imbricate, in about 9 to 14 whorls of ray florets, each with 9 to 11 florets to equal a total of about 120-140 ray florets per inflorescence head, depending on light and temperature conditions. Quantity per Inflorescence head: 120-140. Length: 50 mm. Widths: 22-25 mm. Overall shape: Obovate. Apex shape: Obtuse. Base shape: Acuminate, slightly fused. Margin: Entire. Texture: Glabrous (upper side and underside). Colour when opening fused ray floret starting to show RHS 160D.

*Color*.—Colour when fully opened. Color upper side: RHS 155B to 155C with RHS 1B at small area near the base. Color underside: RHS 155C.

*Disc florets*.—Arrangement: 30-40 yellow-orange disc florets arranged in center of inflorescence head. Quantity per Inflorescence head: 30-40. Length: 8-10 mm. Diameter: 2 mm. Overall shape: Tubular. Apex shape: Star with 5 triangular tips. Base shape: Fused to tube. Color: RHS 17A, RHS 145C near base.

*Phyllary*.—Arrangement: One subtending each floret. Quantity: 120-140. Length: 12-22 mm. Width: 4-6 mm. Overall shape: Rounded. Shape at apex: Acute with rounded tip. Shape at base: Fused. Margin: Entire. Color: Mature: RHS 151B; RHS 146A on underside of the 8-10 phyllaries in the outer whorl. Immature: RHS 151B.

*Bracts*.—Arrangement and appearance: Reflexed, involucral bracts. Quantity: 5. Length: 13-16 mm. Width: 6-8 mm. Overall shape: Subulate. Apex shape: Acute. Base shape: Sessile. Margin: Entire. Texture: Glabrous. Colour mature: Upper side: RHS 137A. Underside: RHS 137A. Colour immature: Upper side: RHS 137A. Underside: RHS 137A.

Reproductive organs:

*Androecium*.—Location: Disc florets only. Stamen number: 5, fused into synandrous tube around style. Stamen length: About 6-10 mm. Anther shape: Tubular. Anther length: About 5-6 mm. Pollen amount: Medium amount. Pollen color: RHS 21A.

*Gynoecium*.—Location: Ray and disc florets. Quantity: 1. Pistil length: 6-10 mm. Stigma shape: Bifurcate. Stigma length: About 2 mm. Stigma color: RHS 151C. Style length: About 4 mm. Style color: RHS 151C. Ovary color: RHS 151C.

Seed/fruit: Seed and fruit production has not been observed.

Disease/pest resistance: Resistance to pathogens and pests common to *Dahlia* has not been observed.

Disease/pest susceptibility: Susceptibility to pathogens and pests common to *Dahlia* has not been observed.

Temperature tolerance: Plants of the new *Dahlia* have exhibited good tolerance to rain, wind and drought; however, flowering may cease during hot periods (temperatures above 25° C.). Low temperature tolerance to 1° C.

Growth regulators: Daminozide (85% water soluble dry concentrate formulation).

What is claimed is:

1. A new and distinct cultivar of *Dahlia* plant named 'DAATTEN', as illustrated and described herein.

* * * * *